United States Patent [19]

Bardy et al.

[11] Patent Number: 4,804,529
[45] Date of Patent: Feb. 14, 1989

[54] USE OF SPECIFIC RELAXATION AGENTS FOR ORGANS OR PATHOLOGIES FOR MODIFYING THE CONTRASTS IN MEDICAL IMAGING BY NUCLEAR MAGNETIC RESONANCE

[75] Inventors: André Bardy, Moranjis; Maria-Louisa Conti, Versailles; Jacques Courtieu, Boulogne; Evelyne Mathieu, Gabriel; Joelle Grzyb, Madame, all of France

[73] Assignee: Commissariat a l'Energie Atomique, Paris, France

[21] Appl. No.: 640,160

[22] Filed: Aug. 10, 1984

[30] Foreign Application Priority Data

Aug. 12, 1983 [FR] France ............... 83 13281

[51] Int. Cl.$^4$ ............................... A61K 49/00
[52] U.S. Cl. ..................... 424/9; 436/173
[58] Field of Search ..................... 424/9; 436/173

[56] References Cited

U.S. PATENT DOCUMENTS

| 3,789,060 | 1/1974 | Goering et al. | 260/429.2 |
| 4,156,683 | 5/1979 | Zehn | 540/465 |
| 4,647,447 | 3/1987 | Gries et al. | 424/9 |

FOREIGN PATENT DOCUMENTS 0071564 2/1983 European Pat. Off. .
M2322 2/1964 France .

OTHER PUBLICATIONS

Chemical Abstracts, vol. 99, No. 7, Aug. 15, 1983, p. 232.
Zanelli et al., British J. of Radiology, vol. 54, (1981), pp. 403–407.
Anderson-Berg et al., J. Nucl. Med., vol. 27, No. 6, (1986), pp. 829–833.
Unger et al., Investigative Radiology, vol. 20, (1985), pp. 693–700.
Curtet et al., Proc. Natl. Acad. Sci. USA, vol. 83, (1986), pp. 4277–4281.

*Primary Examiner*—Richard L. Raymond
*Attorney, Agent, or Firm*—Michael N. Meller

[57] ABSTRACT

The invention relates to specific relaxation agents for organs or pathologies, which can be used for modifying the contrasts in medical imaging by nuclear magnetic resonance.

These agents are constituted by a complex of a paramagnetic element having a biologically active ligand or a ligand coupled to a biologically active molecule and which is specific to an organ or pathology. Thus, they are selectively fixed to the organs and make it possible to modify the contrasts in imaging by nuclear magnetic resonance, due to the presence of the paramagnetic element, which modifies the relaxation times.

For example, when examining the kidney, the complex can be constituted by dimercaptosuccinate or gadolinium diethylene triaminopentaacetate, whilst gadolinium phytate is used in examinations of the liver.

8 Claims, No Drawings

USE OF SPECIFIC RELAXATION AGENTS FOR ORGANS OR PATHOLOGIES FOR MODIFYING THE CONTRASTS IN MEDICAL IMAGING BY NUCLEAR MAGNETIC RESONANCE

The present invention relates to specific relaxation agents for organs or pathologies, usable for modifying contrasts in medical imaging by nuclear magnetic resonance.

Spectroscopy by nuclear magnetic resonance (NMR) was developed in 1946 by Bloch and Purcell and this procedure has been widely used since in the field of physics, organic chemistry and biochemistry for studying the chemical structure of molecules and molecular groups in vitro. The principle of NMR uses the combination of magnetic fields and radiofrequency waves for resonating the nuclei of certain atoms. As one of the most interesting atoms is hydrogen, which is present in the water constituting most of biological tissues (75 to 80% of soft tissues, it is possible to envisage the use of NMR technology in the medical field and over a period of less than 2 years, there has been considerable advances in the development of imaging by nuclear magnetic resonance in this field. The image of the distribution of the protons is obtained from the emitted signal following the resonation of the nuclei, and the reconstruction of the computer leads to the display of sagittal, frontal and cross-sections of the human body.

The analysis of the resonant frequencies and that of the characteristic parameters of the nuclei is obtained by NMR spectrometry. This is the observation of the pulse response of the nuclei to excitation by a radiofrequency wave. The nuclei return to their initial state of equilibrium according to time constants depending on their environment and are called relaxation times.

The relaxation time $T_1$ (called the spin lattice) characterizes the behaviour of the nucleus observed in the surrounding magnetic field (modified by neighbouring electrons and nuclei). The relaxation time $T_2$ (spin - spin) is characteristic of molecular bonds in which the observed nucleus is involved. Its modification translates microscopic movements of this nucleus with respect to adjacent nuclei.

Another parameter which can be measured is the density $\rho$ of the protons in the medium. As a first approximation, it represents the quantity of free water contained in the sample. It would therefore appear that the density of the water in the tissue, but also the relative mobility of the water molecules induce variations of the measured parameters, which is encountered in pathological conditions, but can also be brought about by the introduction of elements modifying the surrounding medium.

At present, the image by nuclear magnetic resonance represents the distribution of these parameters $\rho$, $T_1$, $T_2$ or their combination. The contrast between a given tissue and the adjacent tissues increases as a function of the tissues containing more or less water or mobile protons and the relaxation times differing. It is also possible to modify the contrast by varying one or more of these parameters. Experience has shown that it was of greater interest to modify the relaxation time to improve the contrast of the image. Thus, the density of the protons (in practice those of water and greases) varies little between individual organs and often less between normal and pathological tissues. However, the relaxation characteristics are dependent on a large number of factors (microscopic dynamics of the molecules, chemical exchange, paramagnetic disturbances, etc), which are much more variable. The at least relative technical possibilities of selecting different parameters for obtaining the final image (experimentally echoes of spins aiding the function of $T_2$, or experimentally reversal - recovery of the magnetization permitting the local measurement of $T_1$) have shown the significane of the method. The most spectacular example is that of the possible contrast between the white substance and the grey substance on the images of the normal or pathological brain.

Despite the importance of natural phenomena, the contrast can still be inadequate, particularly between healthy and pathological tissues within the same or organ or for revealing anatomical compartments such as the urinary passages, the biliary ducts etc. Consideration has also been given to the artificial accentuation of the contrast by introducing into the organism to be examined elements which modify in particular the magnetic field, e.g. paramagnetic compounds, in order to disturb the relaxation times of the nuclei already present in the organism, by adding to the nuclear relaxation a component linked with disturbances by an electron magnetic moment.

The use of contrast media of this type is in particular described by Brasch, Runge et al in Radiology, Vol. 147, No. 3, June 1983, pp. 773–791. These contrast media can be gadolinium or transition metal salts, nitroxide radicals or chrome ethylene diamine tetraacetate.

However, use of such contrast media is not satisfactory, because it is necessary to inject into the organisms a relatively large quantity of the product, in order to obtain the sought effect in the examined organ. Therefore, numerous agents cannot be used, because they do not make it possible to obtain a significant improvement of the NMR signal at non-toxic doses.

The present invention relates to novel relaxation agents making it possible to modify contrasts in medical imaging by nuclear magnetic resonance, whilst obviating the aforementioned disadvantage.

The present invention relates to a relaxation agent which can be used for modifying contrasts in medical imaging by nuclear magnetic resonance, wherein it comprises a complex of a paramagnetic element chosen from among the lanthanides and the transition metals carrying the atomic numbers 21 to 29, 42 and 44, having a biologically active ligand or a ligand coupled to a biologically active molecule specific of an organ or a pathology, said ligand being chosen from among:

(1) amides in accordance with the formula:

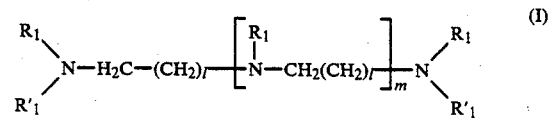

(I)

in which $R_1$ and $R'_1$, which can be the same or different represent: $CH_2-(CH_2)_1-NH_2$ with 1 being a number between 1 and 7, $CH_2-PO_3H_2$ an amino acid residue, the radical of formula $-R_2-COOH$ with $R_2$ representing an alkylene or alkenylene radical having 1 to 18 carbon atoms, the radical of formula:

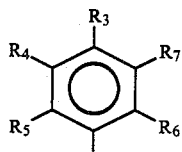

with $R_3, R_4, R_5, R_6$ and $R_7$, which can be the same or different, representing a $C_1$ to $C_8$ alkyl, H, SH, OH, $COOR_8$ with $R_8$ representing a hydrogen atom or a physiologically acceptable metal, an amino acid residue $CH_2PO_3H_2$

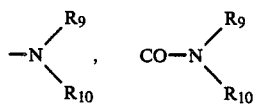

with $R_9$ and $R_{10}$, which can be the same or different, representing H or a $C_1$ to $C_4$ alkyl radical and m a number between 0 and 4;

(2) tetra-aza compounds for formula:

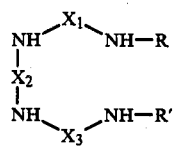 (II)

in which $X_1$, $X_2$ and $X_3$, which can be the same or different, represent alkylene radicals with 2 to 4 carbon atoms which are either not substituted or are substituted by at least one of the following groups: $C_1$ to $C_8$ alkyl, $COOR_8$ with $R_8$ representing a hydrogen atom or a physiological acceptable metal, OH, SH an amino acid residue $CH_2PO_3H_2$,

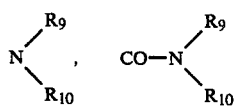

with $R_9$ and $R_{10}$ representing hydrogen or a $C_1$ to $C_4$ alkyl radical, and in which R and R', which can be the same or different, represent a hydrogen atom, a methyl or an ethyl radical or in which R and R' together form an alkylene radical with 2 to 4 carbon atoms, which is not substituted or is substituted by at least one of the following groups: $C_1$ to $C_8$ alkyl, $COOR_8$ with $R_8$ representing a hydrogen atom or a physiologically acceptable metal OH, SH, an amino acid residue $CH_2PO_3H_2$,

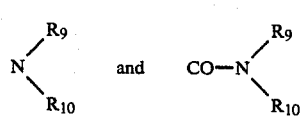

with $R_9$ and $R_{10}$ representing hydrogen or a $C_1$ to $C_4$ alkyl radical;

(3) tetra-aza compounds of formula:

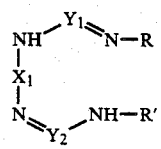 (III)

in which $X_1$ represents an alkylene radical with 2 to 4 carbon atoms, which is not substituted or is substituted by at least one of the following groups: $C_1$ to $C_8$ alkyl, $COOR_8$ with $R_8$ representing a hydrogen atom or a physiologically acceptable metal, OH, SH, and amino acid residue $CH_2PO_3H_2$,

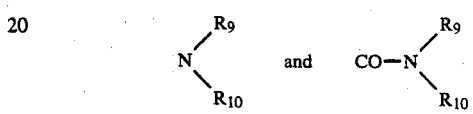

with $R_9$ and $R_{10}$ representing hydrogen or a $C_1$ to $C_4$ alkyl radical, $Y_1$ and $Y_2$, which can be the same or different, representing a trivalent radical chosen from among 1-ethanyl-2-ylidene, 1-propanyl-3-ylidene and 1-butanyl-4-ylidene, unsubstituted or substituted by at least one of the following groups: $C_1$ to $C_8$ alkyl, $COOR_8$ with $R_8$ representing a hydrogen atom or a physiologically acceptable metal OH, SH, an amino acid residue, $CH_2PO_3H_2$,

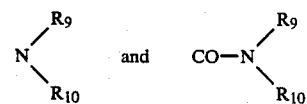

with $R_9$ and $R_{10}$ representing hydrogen or a $C_1$ or $C_4$ alkyl radical and in which R and R', which can be the same or different, represents a hydrogen atom, a methyl or an ethyl radical, or in which R and R' together form an alkylene radical with 2 to 4 carbon atoms, which is unsubstituted or is substituted by at least one of the following groups: $C_1$ to $C_8$ alkyl, $COOR_8$ with $R_8$ representing a hydrogen atom or a physiologically acceptable metal, OH, SH, an amino acid residue, $CH_2PO_3H_2$,

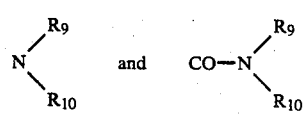

with $R_9$ and $R_{10}$ representing hydrogen or a $C_1$ to $C_4$ alkyl radical;

(4) porphyrins in accordance with the formula:

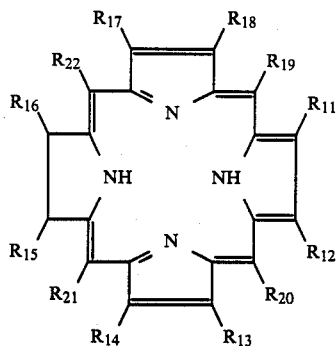
(IV)

in which $R_{11}$, $R_{12}$, $R_{13}$, $R_{14}$, $R_{15}$, $R_{16}$, $R_{17}$ and $R_{18}$ which can be the same or different represent H, a $C_1$ to $C_4$ alkyl, a $C_2$ to $C_4$ alkenyl, CHOH-$R_9$ with $R_9$ representing hydrogen or a $C_1$ to $C_4$ alkyl radical $(CH_2)_n COOR_9$, $(CH_2)_n OH$, $(CH_2)_n$-SH,

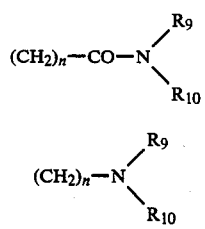

with n being a number between 1 and 4, $R_9$ and $R_{10}$, which can be the same or different, representing a hydrogen atom or a $C_1$ to $C_4$ alkyl radical, and $R_{19}$, $R_{20}$, $R_{21}$ and $R_{22}$, which can be the same or different, representing H, a phenyl radical, a pyridyl radical, or a radical of formula

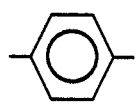

$SO_3R_8$ with $R_8$ representing a hydrogen atom or a physiologically acceptable metal;

(5) hexaphosphoric myo-inositol acid of formula:

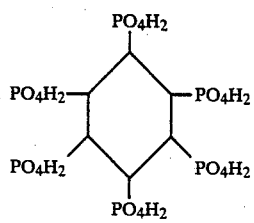
(V)

(6) derivatives of formula:

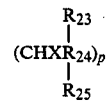

in which $R_{23}$ and $R_{25}$, which can be the same or different, represent $CH_2$—$COOR_8$, $COOR_8$ with $R_8$ representing a hydrogen atom or a physiologically acceptable metal, or $CH_2OH$, X representing O or S, $R_{24}$ representing H or $COOR_8$ with $R_8$ representing a hydrogen atom or a physiologically acceptable metal, and p is a number between 1 and 6;

(7) phosphines of formula:

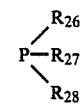
(VII)

in which $R_{26}$, $R_{27}$ and $R_{28}$, which can be the same or different, represent a $C_1$ to $C_4$ alkyl radical, $(CH_2)_9$—$COOR_8$ with $R_8$ representing a hydrogen atom or a physiologically acceptable metal, $(CH_2)_q OH$, $(CH_2)_q$-$PO_3H_2$,

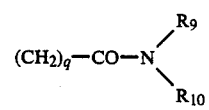

with q being a number between 1 and 18 and $R_9$ and $R_{10}$ representing a hydrogen atom or a $C_1$ to $C_4$ alkyl radical;

(8) polycarboxylic amino acids of formula:

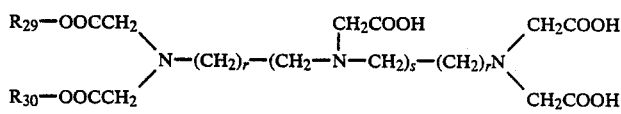

in which r is a number between 1 and 4, s is a number between 0 and 2, and $R_{29}$ and $R_{30}$ represent a hydrogen atom or $R_{29}$ and $R_{30}$ together represent Ca, provided that $R_{29}$ and $R_{30}$ do not represent H when s is equal to 0 to 1 and the ligand is not coupled to a biologically active molecule;

(9) phenylcarbamoyl-methyliminodiacetates, substituted or not substituted on the phenyl nucleus by $C_1$ to $C_4$ alkyl radicals;

(10) bleomycins;

(11) bleomycins coupled to an organic complexing agent;

(12) macrocyclic diaza compounds of formula:

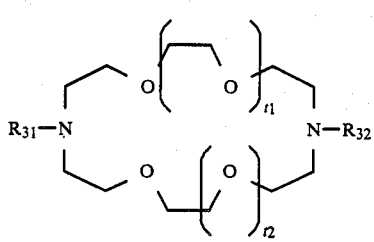

(IX)

in which $t_2$ and $t_2$, which can be the same or different, are numbers between 0 and 2 and in which the groups $R_{31}$ and $R_{32}$, which can be the same or different, represent a hydrogen atom, $(CH_2)_n$—$COOR_8$, with $R_8$ representing a hydrogen atom or a physiologically acceptable metal, $(CH_2)_nSH$, $(CH_2)_nOH$,

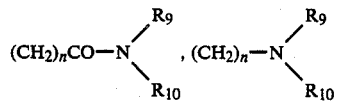

with $R_9$ and $R_{10}$, which can be the same or different representing a hydrogen atom or a $C_1$ to $C_4$ alkyl radical and n being an integer between 1 and 4, or in which $R_{31}$ and $R_{32}$ can together form the radical —$CH_2$—$CH_2$—$O$—$(CH_2$—$CH_2$—$O)_{t3}$—$CH_2$—$CH_2$— with $t_3$ number between 0 and 2, the different carbon atoms of the diaza compound also being substitutable by one or more radicals chosen from among $(CH_2)_n$—$COOR_8$, $(CH_2)_n$—$SH$, $(CH_2)_nOH$,

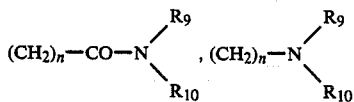

with $R_9$ and $R_{10}$, which can be the same or different, representing a hydrogen atom or a $C_1$ to $C_4$ alkyl radical and n being a number between 1 and 4;

(13) enterobactin according to formula:

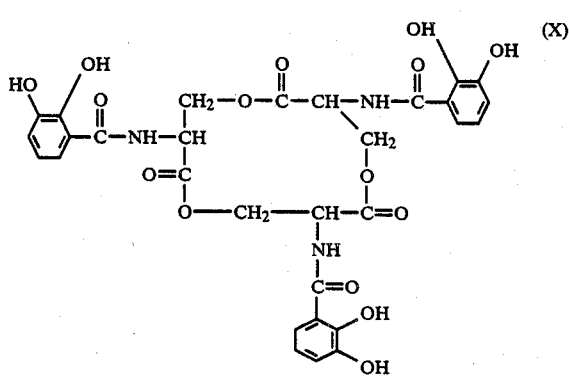

(14) the carbocyclic analog of enterobactin of formula:

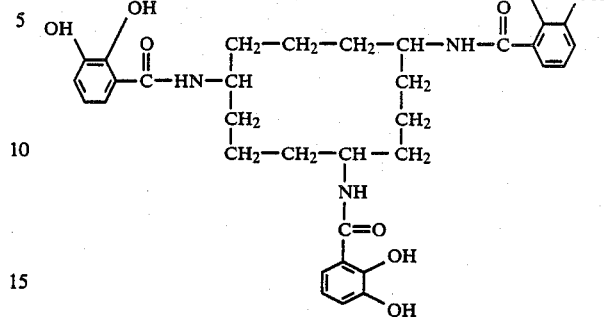

(15) the carbocyclic derivative of formula:

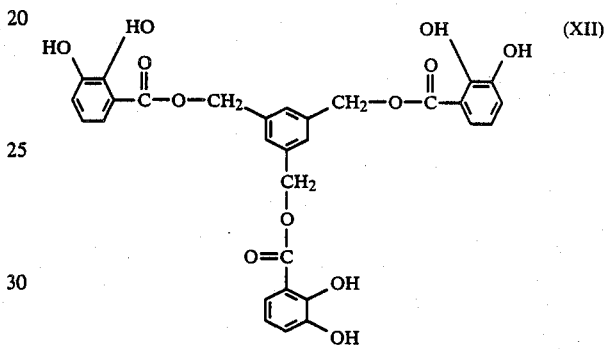

(16) siloxans of formula:

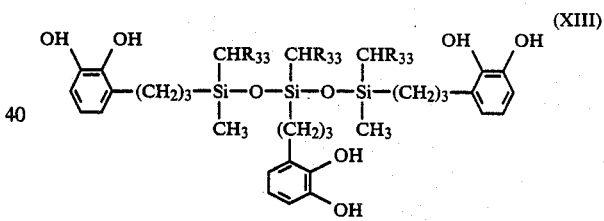

in which $R_{33}$ represents a hydrogen atom, a methyl group or the group —$CH_2$—$C_6H_4OCH_2COOH$.

It is pointed out that in the lanthanide series, the following elements are paramagnetic: cerium, praseodymium, neodymium, promethium, samarium, europium, gadolinium, terbium, dysprosium, holmium, erbium and thulium.

According to the invention, preference is given to the paramagnetic lanthanide being chosen from among gadolinium, dysprosium, holmium, thulium, terbium and samarium. Among the latter elements, particular preference is given to gadolinium.

The relaxation agents according to the invention have in particular the advantage of being able to modify the contrast of an NMR image due to the presence of the paramagnetic element constituted by lanthanide or a transition metal and of being selectively fixable to the organ to be examined, due to the choice of ligands. It is therefore possible to reduce by a significant factor, the quantity of the injected agent and to reduce the toxicity risks. Thus, the relaxation agent has a vector part constituted by the biologically active ligand, which is specific to the organ or pathology to be examined and it is fixed by this vector part to the organ or area to be investigated.

Once fixed, it improves the contrast of the NMR image due to the presence of the paramagnetic element.

The use of paramagnetic lanthanide complexes makes it possible to obtain the sought result, despite combining the paramagnetic element with a vector molecule. Thus, in this case, the paramagnetic effect of the lanthanide on the relaxation times of the proton is neither cancelled out, nor excessively reduced by the presence of the molecules or the biologically active ligand. In the same way, the biologically active ligand retains its properties and its selective fixation to the organ or area to be examined is not disturbed by the paramagnetic element.

According to the invention, the ligand of the complex is chosen as a function of the organ or area of the human body to be studied in order to obtain a good fixation of the complex to the parts to be observed.

The aforementioned biologically active ligands can have different substituents and the choice of the latter in particular makes it possible to give thereto the desired specificity with respect to the organ or pathology to be studied.

According to the invention, it is in particular possible to give the ligand of the complex the desired specificity by coupling the same to a biologically active molecule e.g. chosen from among the antigens, antibodies, monoclonal antibodies, fragments and AC-fragment combinations, drugs, acceptors, steriods, amino acids, peptides and enzymes. It is more particularly possible to use a monoclonal antibody. Monoclonal antibodies which can be used can be obtained by the process described by Milstein and Kohler in Nature, Vol. 256, pp. 495–497, 1975. This process essentially involves injecting an immunogen into a mouse or another suitable animal. The mouse is then killed and the cells taken from the spleen are combined with the myeloma cells.

This gives a hybrid cell called a "hybridome", which reproduces in vitro. The population of hybridomes is selected and manipulated so as to isolate the individual clones, each of which produces a single antibody species relative to an antigen. This individual specific antibody obtained in this way is the product of a single cell B of the immune animal, produced in response to a specific antigenic site recognised on the immunogenic substance.

The coupling a monoclonal antibody to the ligand can be brought about e.g. via acid, amine, phenol, hydroxyl or ketone functions of the antibody or ligand and preferably via an amine or acid function, using the conventional coupling reactions and reagents such as carbo-diimides, glutaraldehyde, benzidine, mixed anhydrides, active esters of the antibody and paraaminophenyl acetic acid.

In order to carry out this reaction, the ligand must have reactive groups such as:

—NCS

O

S

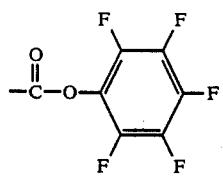

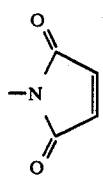
—NH—C—CH$_2$Br

—C—N
‖
O

—SO$_2$Cl

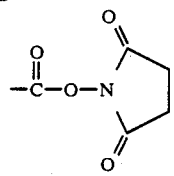
—C—O—N

—N—SO$_2$—CH=CH$_2$

—N$_2^+$ from —NH$_2$

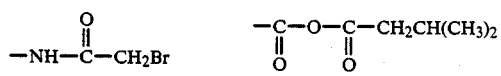

The latter can be supplied to the ligand by conventional methods.

The biological specificity can also be given to the ligand by the use of groups such as amino acid residues, i.e. radicals derived from an amino acid by removing a hdyrogen atom from an alkyl radical, a hydroxyl from the COOH group or a hydrogen from the NH$_2$ group of the amino acid.

The amino acid can in particular be natural amino acids, such as glycocoll, alanine, phenylalanine, leucine, asparagine, glutamine, lysine, serine, cystine and tyrosine.

When it is wished to obtain an image of the brain or study the pathology of the latter, it is possible to use complexes constituted by gluconates, dicitrates or polycitrates of paramagnetic lanthanides or paramagnetic lanthanide and calcium diethylene triaminopentacetate. For complexes constituted by gluconates and dicitrates, the ligand complies with formula VI and with R$_{23}$ and R$_{25}$ representing CH$_2$—COOH, X representing O, R$_{24}$ representing COOH and p=1 in the case of the citrate. In the case of lanthanides and calcium diethylene triaminopentaacetate, the ligand complies with formula VIII with r and s equal to 1. These complexes can also be obtained by the action of the corresponding acid on a paramagnetic lanthanide salt or oxide.

For the study of the heart, it is possible to use complexes also having trialkyl phosphines of formula VII as the ligands.

When it is wished to obtain an image of the kidney, use is advantageously made of complexes constituted by gluconates, dimercaptosuccinates or thiomalates or paramagnetic lanthanides, paramagnetic lanthanide and calcium diethylene triaminopentaacetate or lanthanide triethylene tetraminohexaacetate. These complexes are also obtained by the reaction of the corresponding acid on a paramagnetic lanthanide salt or oxide.

When it is wished to obtain an image of the biliary ducts, use is advantageously made of a complex constituted by a paramagnetic lanthanide phenylcarbamoyl methyl iminodiacetate, which may or may not be substituted on the phenyl nucleus.

When studying the liver, use can be made of a paramagnetic lanthanide phytate or a lanthanide myo-inositol hexaphosphate of formula V.

For the study and detection of tumors, it is possible to use complexes of lanthanides in which the biologically active ligand is a porphyrin or a bleomycin.

Porphyrins or derivatives of porphin have the general structure:

for a pathology, because they also have an affinity for tumors.

Bleomycins can directly complex paramagnetic langthanides, but it is also possible to obtain a relaxation agent by firstly coupling a bleomycin with an organic complexing agent having several complexing sites, such as an aminopolycarboxylic acid, such as diethylene triaminopentaacetic acid, triethylene tetraminohexaacetic acid or ethylene diaminotetraacetic acid and by then complexing the paramagnetic lanthanides by means of the complexing agent coupled to the bleomycin.

The formula of bleomycin is given hereinafter:

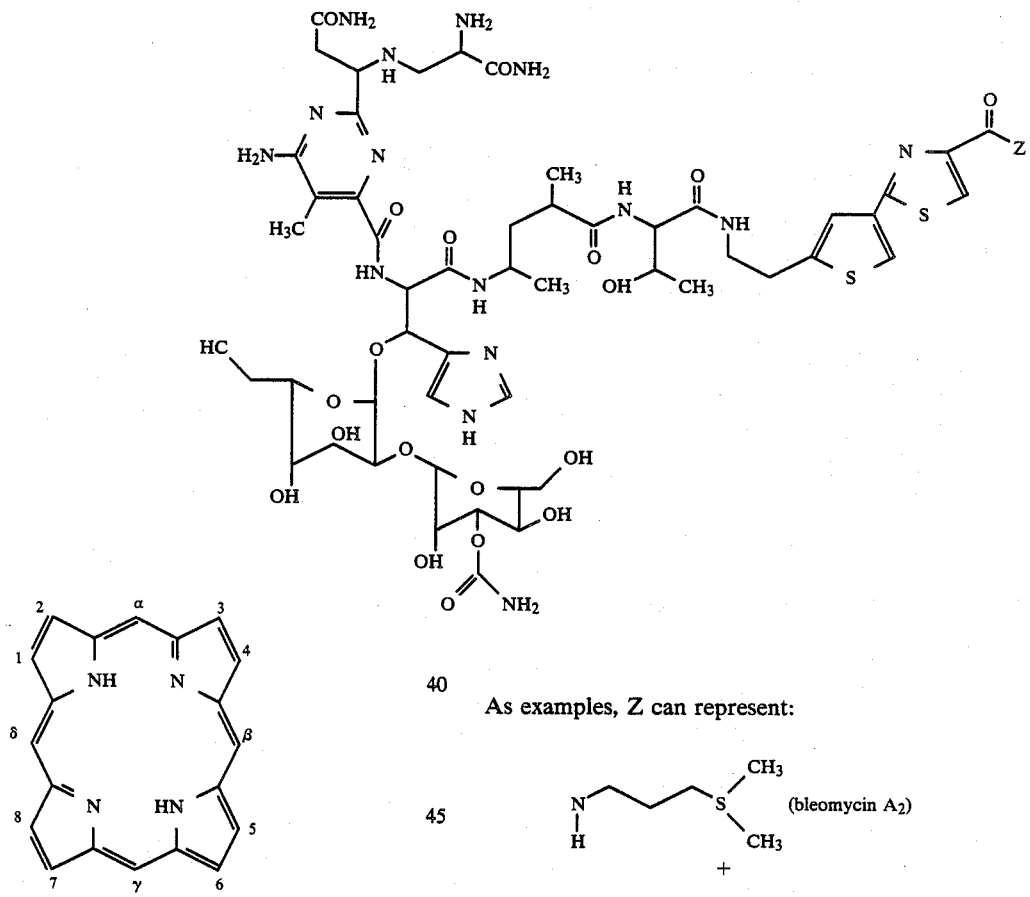

It is possible to obtain several hydrosoluble derivatives by carrying out substitutions in alpha, beta, gamma and/or delta.

An example of a hydrosoluble derivative is sulphonated tetraphenyl porphyrin, i.e. the porphyrin of formula IV in which $R_{19}$, $R_{20}$, $R_{21}$ and $R_{22}$ represent the radical:

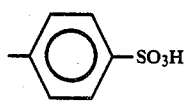

and in which $R_{11}, R_{12}, R_{13}, R_{14}, R_{15}, R_{16}, R_{17}$ and $R_{18}$ represent a hydrogen atom.

By complexing these hydrosoluble derivatives by a paramagnetic lanthanide, agents are obtained which have a strong tumoral affinity.

Bleomycins are more important molecules, which can complex lanthanides and which have a specificity As examples, Z can represent:

Generally, use is made of paramagnetic lanthanide complexes according to the invention in the form of sterile, apyrogenic solutions, e.g. in the form of a solution in physiological serum and they are intravenously, intrachidially or orally injected. The injected doses are generally low and are chosen as a function of the toxicity of the product, so as to obtain an optimum modification of the contrast without causing toxicity.

Thus, in the case of gadolinium dimercaptosuccinate, the injected does can correspond to 0.6 μmol of gadolinium and 1.8 μmol, of dimercaptosuccinate per 200g of body weight. This is well below the dose, where there is an acute toxicity effect due to the gadolinium and which is 29.6 μmol of gadolinium per 200 g, or 55mg of gd/kg. Moreover, the injected dose is chosen as a function of the fixation level of the complex on the organ to be examined and the size of the latter, whilst taking account of the toxicity.

Following the injection of the product, it is necessary to wait until the fixation level thereof on the organ to be examined has reached its maximum. This maximum can vary as a function of the nature of the complex used. Thus, in the case of gadolinium phytate, the fixation level of the complex on the kidney is approximately 80% and is reached after about 5 to 30 minutes. In the case of gadolinium dimercaptosuccinate, a maximum fixation level of 15% on the kidney is obtained after 2 hours.

On reaching this maximum fixation level, it is possible to make an image of the organ to be examined by nuclear magnetic resonance using conventional equipment.

The specificity of the relaxation agents according to the invention can be further improved by conditioning them in an appropriate form. Thus, they can be used as colloids suspended in an aqueous solution, which makes it possible to fix them in preferential manner to the glands of the lymphatic system or the hepatic system, as a function of the particle size distribution of the colloid. Thus, complexes such as citrates of lanthanides conditioned in colloidal form, e.g. with a particle size of approximately 10 nm, in the presence of stabilizers such as polyvinylpyrrolidone or gelatin, can be used in an appropriate galenic form for indirect lymphography by subcutaneous injection of the suspension.

It is also possible to include complexes of lanthanides according to the invention in liposomes and in this way obtain relaxation agents having a greater affinity for the liver, spleen and certain tissues. This can be carried out by conventional processes, such as those described in Labo-Pharma-Problèmes et Techniques, No. 281, November, 1978, pp.905 to 907; Presse Mèdicale, May 12th, 1979, 8, No.21, pp.1749 to 1752 and Journal Français de Biophysique et Medecine Nuclèaire, 1, 1979, 3 (1), pp, 3 to 12.

The following examples serve to illustrate the invention in a non-limitative manner.

EXAMPLE 1

This example relates to the preparation of gadolinium dimercaptosuccinate and its use for obtaining an image of the kidney by nuclear magnetic resonance.

Dimercaptosuccinic acid is dissolved in water to which has been added a few drops of soda, whilst ensuring that the pH does not exceed 2.5. A gadolinium chloride solution is then added to the aforementioned solution, so as to obtain a dimercaptosuccinic acid/$Gd^{3+}$ molar ratio of 3:1, a dimercaptosuccinic acid concentration in the final solution of the most equal to 6 mmol. $1^{-1}$ and a gadolinium concentration at the most equal to 2 mmol. $1^{-1}$. The pH is adjusted to 2.5 and the product is kept protected from light at 4° C. in an inert atmosphere.

It was established that the product obtained gives a widening of the proton peak, which is inversely proportional to the relaxation time $T_2$ of 4h in solution at 1mmol.$1^{-1}$ (the width of the peak of the protons in the water is approximately 1Hz).

Thus, the effect of the gadolinium dimercaptosuccinate is substantially identical to that of the $Gd^{3+}$ ion, which gives a widening of 4.5 Hz in a 1mmol.$1^{-1}$ solution.

0.2 cc of the solution obtained is injected into rats weighing 200g, this corresponding to a dose of 0.6 μmol of gadolinium and 1.8 μmol of dimercaptosuccinic acid. After 90 minutes, the rats are killed and their kidneys removed. The kidneys removed are examined by NMR using the BRUKER WP 60 apparatus, whose NMR spectrum by Fourier transform in the presence of a static field gradient on z gives projection in sections of the investigated organ.

Under these conditions, there is a variation of the relaxation time $T_1$, which locally reaches 50% and on an overall basis 15% for the complete kidney. Moreover, it is found that gadolinium dimercaptosuccinate is 30% fixed to the two kidneys.

EXAMPLE 2

This example relates to the preparation of gadolinium phytate. A 20 mmol.$1^{-1}$ solution of phytic acid is prepared by treating a sodium phytate solution with a cationic resin AG 50×8 with a particle size smaller than 0.038mm (400 mesh), so that a solution is obtained with a pH of 1.8. Hexahydrated gadolinium chloride is dissolved in distilled water and to this solution is added a phytic acid quantity such that the $Gd^{3+}$ phytic acid molar ratio is 1:6. The pH is then adjusted to 4.8 and the solution diluted to obtain the desired concentration, which is generally below 3 mmol.$1^{-1}$.

It was established that this product gives a widening of the peak of the protons in the water which is inversely proportional to the relaxation time $T_2$ of 16 Hz for a 1mmol.$1^{-1}$ solution. Thus, the effect of this complex is superior to that of ionic gadolinium (4.5 Hz in 1mmol.$1^{-1}$ solution).

This product is used for studying the liver, to which it is fixed by more than 80%.

After intravenously injecting into rats 0.0017 mmol of gadolinium phytate and waiting 20 to 30 minutes, the rates are killed and the livers removed after dissecting. The in vitro measurement of the $T_s$ of rat liver fragments revealed that the gadolinium phytate injection caused a roughly 17% $T_s$ reduction.

EXAMPLE 3

This example relates to the preparation of calcium and gadolinium diethylene triaminopentaacetate. 2.5g of $Gd_2O_2$ and 5g of diethylene triaminopentaacetic acid are suspended in 60ml of water. The suspension is stirred for approximately 48 hours at approximately 50° C. The diethylene diaminopentacetic acid slowly dissolves the gadolinium oxide. Dilution takes place to 100ml and acetone is added to precipitate the gadolinium complex formed. Filtration takes place protected from moisture and the precipitate is dried in vacuo in a desiccator with calcium chloride.

The thus obtained precipitates is agin dissolved in distilled water and treated hot (approximately 80° C.) with a calcium carbonate suspension, whilst stirring for 24 hours. The excess calcium carbonate is filtered and the mixed gadolinium and calcium diethylene triaminopentacetate salt is precipitated by an acetone excess, followed by the drying of the precipitate in vacuo.

The measurement of the $LD_{50}$ of this product on 6 groups of 5 male mice and on 6 groups of 5 female mice gave the following results:
$LD_{50}=900\pm82.7$ mg/kg for the male mice,
$LD_{50}=1158\pm92.3$ mg/kg for the female mice,
$LD_{50}=479$ mg/kg.

Thus, this corresponds to a LD$_{50}$ of a 1.65 mmol/kg. The mixed salt is soluble in water and the pH is 6.8.

The product obtained gives a widening of the peak of the proton in water, which is inversely proportional to the relaxation time T$_2$ of 3.4 Hz in a 1mmol.1$^{-1}$ solution.

This product can be used for studying abnormalities of the perfusion of organs such as the kidney, brain, etc.

EXAMPLE 4

This example relates to the preparation of a macrocyclic amine gadolinium complex.

Equimolar quantities of GdCl$_3$ and macrocyclic amine constituted by "Cyclam", or 1,4,8,11-tetraazacyclodecane are separately dissolved in methanol. 2mmol of anhydrous GdCl$_3$ dissolved in methanol are mixed with 2 mmol of "Cyclam" also dissolved in methanol whilst mixing the two solutions and heating them to reflux for approximately 3 hours. The solution is filtered and the complex precipitated with ether, followed by the drying of the precipitate in vacuo. The measurement of the relaxation time T$_1$ for solutions ranging between 5 and 0.2 mmol gives a 1/20 to ¼ reduction compared with water.

EXAMPLE 5

This example relates to the preparation of a gadolinium complex labelled by monoclonal antibodies marketed under reference 19.9. This monoclonal antibody is specific of human colorectal cancers and this synthesis was carried out by using fragment Fab'$_2$ of the antibody.

20mg of antibody, i.e. 2.10$^{-7}$ mol, were coupled in solution in 0.1M sodium bicarbonate at pH 8 with 40.10$^{-7}$ mol of DTPA (diethylene triaminopentaacetate) anhydride dissolved in dimethylsulphoxide. This represents a DTPA/antibody molar ratio of 20. Coupling takes place in 15 minutes, accompanied by stirring at ambient temperature.

The antibody coupled to the DTPA is purified by filtration on a Sephadex G100 column (12 x 2.5 cm). The antibody quantity coupled to the DTPA is determined after measurement of the optical density at 280 nm. It is known that under these coupling conditions, 8 molecules of DTPA are coupled per antibody molecule, i.e. 16.10$^{-7}$ mol of DTPA for 2.10$^{-7}$ mol of antibody.

Complexing of the gadolinium to the antibody coupled to the DTPA takes place in the following way. 16.10$^{-7}$ mol of gadolinium chloride dissolved in distilled water are added to the solution containing the antibody coupled to the DTPA. The gadolinium/DTPA ratio is consequently 1. Complexing takes place for 1 hour accompanied by stirring at ambient temperature. The gadolinium - antibody complex formed in purified by means of DTPA by filtering on a Sephadex G100 column (10×1.5 cm).

The gadolinium - antibody via DTPA complex is recovered and after determining the antibody quantity complexed to the gadolinium by measuring the optical density at 280nm, the complex is kept at +4° C.

Thus, a gadolinium - DTPA - antibody complex is obtained, whose antibody concentration (20 mg/ml) and gadolinium concentration (10$^6$ mol/ml) are known. This product gives a widening of the peak of the proton in the water, which is inversely proportional to the relaxation time T$_2$ of 2.9 Hz in a 1 mmol.1$^{-1}$ solution.

EXAMPLE 6

Preparation of gadolinium cryptates in which the ligand is in accordance with the following formulas:

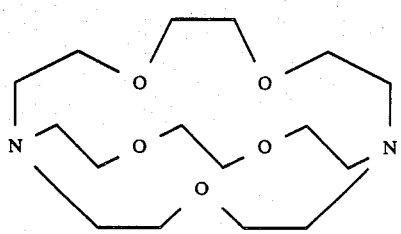

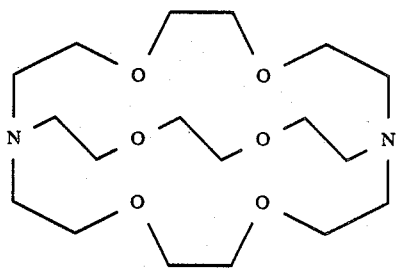

0.5 mmol of cryptate and 0.5 mmol of anhydrous gadolinium chloride are dissolved in 60ml of anhydrous methanol. Anhydrous reflux boiling takes place for 4 hours in an inert atmosphere. The volume of the solvent is then evaporated to approximately 40ml and the complex is precipitated with dry ether. The product is filtered and dried in vacuo. These gadolinium complexes give a widening of the peak of the proton, which is inversely proportional to the relaxation time T$_2$ of 2.8 Hz for a mmol/litre solution.

EXAMPLE 7

This example relates to the preparation of gadolinium triethylene tetraaminohexaacetate.

Equimolar quantities of gadolinium oxide and triethylene tetraaminohexaacetic acid are mixed in water and heating takes place at approximately 90° C. until dissolved. This is followed by cooling and precipitation of the complex with excess acetone. The product is filtered and dried in vacuo. This product, which contains 2 atoms of gadolinium per molecule, has a widening of the proton peak, which is inversely proportional to the relaxation time T$_2$ of 8 Hz for a 1 mmol/litre solution.

What is claimed is:

1. A diagnostic process consisting of examining certain organs by nuclear magnetic resonance, which comprises: (a) introducing into the organism of a patient to be examined a contrast-modifying, non-toxic dosage amount of a relaxation agent consisting of a complex of a paramagnetic element selected from the group consisting of lanthanides and transition metals having atomic numbers 21 to 29, 42 and 44, and a biologically active ligand or a ligand coupled to a biologically active molecule specific of an organ or a pathology, and said liquid being selected from the group consisting of:

macrocyclic diaza compounds of formula:

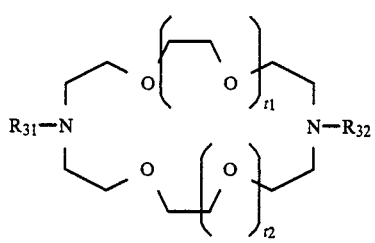
(IX)

in which $t_1$ and $t_2$, which can be the same or different, are numbers between 0 and 2 and in which the groups $R_{31}$ and $R_{32}$, which can be the same or different, represent a hydrogen atom, $(CH_2)_n$—$COOR_8$, with $R_8$ representing a hydrogen atom or a physiologically acceptable metal, $(CH_2)_n SH$, $(CH_2)_n OH$,

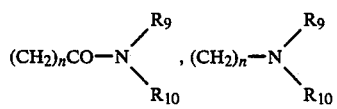

with $R_9$ and $R_{10}$, which can be the same or different, representing a hydrogen atom or a $C_1$ to $C_4$ alkyl radical and n being an integer between 1 and 4, or in which $R_{31}$ and $R_{32}$ can together form the radical —$CH_2$—$CH_2$—$O$—$(CH_2$—$CH_2$—$O)_{t_3}$—$CH_2$—$CH_2$— with $t_3$ number between 0 and 2, the different carbon atoms of the diaza compound also being substitutable by one or more radicals chosen from among $(CH_2)_n$-$COOR_8$, $(CH_2)_n$-$SH$, $(CH_2)_n OH$,

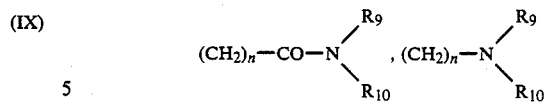

with $R_9$ and $R_{10}$, which can be the same or different, representing a hydrogen atom or a $C_1$ to $C_4$ alkyl radical and n being a number between and 1 and 4; and (b) producing an image of the organ or organs to be examined by nuclear magnetic resonance.

2. A method of claim 1 wherein the ligand is a cryptate.

3. A method of claim 1, wherein the hepatic function of the lymphatic system is examined and the complex of the paramagnetic element is in the form of a colloid suspended in an aqueous solution.

4. A method of claim 1, wherein the complex of the paramagnetic element is included in liposomes.

5. A method of claim 1, wherein the ligand is coupled to a biologically active molecule selected from the group consisting of monoclonal antibodies fragments of monoclonal antibodies and combinations hereof.

6. A method of claim 2, wherein the ligand is coupled to a biologically active molecule selected from the group consisting of monoclonal antibodies fragments of monoclonal antibodies and combinations hereof.

7. A process according to claim 1, wherein the lanthanide is selected from the group consisting of gadolinium, dysprosium, holmium, thulium, terbium and samarium.

8. A process according to claim 1, wherein the paramagnetic element is gadolinium.

* * * * *